United States Patent
James et al.

(10) Patent No.: US 11,365,321 B2
(45) Date of Patent: Jun. 21, 2022

(54) CORROSION INHIBITING COATING ADDITIVE

(71) Applicant: Battelle Memorial Institute, Columbus, OH (US)

(72) Inventors: Joshua P. James, Columbus, OH (US); Ramanathan S. Lalgudi, Westerville, OH (US)

(73) Assignee: Battelle Memorial Institute, Columbus, OH (US)

( * ) Notice: Subject to any disclaimer, the term of this patent is extended or adjusted under 35 U.S.C. 154(b) by 161 days.

(21) Appl. No.: 16/347,247

(22) PCT Filed: Nov. 4, 2017

(86) PCT No.: PCT/US2017/060067
§ 371 (c)(1),
(2) Date: May 3, 2019

(87) PCT Pub. No.: WO2018/085735
PCT Pub. Date: May 11, 2018

(65) Prior Publication Data
US 2019/0256719 A1    Aug. 22, 2019

Related U.S. Application Data

(60) Provisional application No. 62/417,578, filed on Nov. 4, 2016.

(51) Int. Cl.
| | | |
|---|---|---|
| C09D 5/08 | (2006.01) | |
| C09D 175/04 | (2006.01) | |
| C07C 309/39 | (2006.01) | |
| C08K 5/42 | (2006.01) | |

(52) U.S. Cl.
CPC ............ *C09D 5/086* (2013.01); *C07C 309/39* (2013.01); *C09D 5/084* (2013.01); *C09D 175/04* (2013.01); *C07C 2601/16* (2017.05); *C08K 5/42* (2013.01)

(58) Field of Classification Search
CPC .................................................. C07C 309/39
See application file for complete search history.

(56) References Cited

FOREIGN PATENT DOCUMENTS

| CN | 10233017 A | 2/2012 |
|---|---|---|
| EP | 2915903 A1 | 9/2015 |
| WO | 2008076637 A1 | 6/2008 |

OTHER PUBLICATIONS

Machine translation of CN 102337017 (Year: 2012).*
Gaca et al (Studies of the kinetics of the reaction of chlorine in derivatives of 4,4'-dichlorodiphenyl sulfone, BTN, Annals of the Department of Technical Sciences, Series A, 1980, No. 14, 41-5). (Year: 1980).*
Translation of Gaca et al (Studies of the kinetics of the reaction of chlorine in derivatives of 4,4'-dichlorodiphenyl sulfone, BTN, Annals of the Department of Technical Sciences, Series A, 1980, No. 14, 41-5). (Year: 1980).*
Written Opinion and International Search Report from corresponding PCT application No. PCT/US2017/060067, dated Feb. 26, 2018.
He, Jihui, Polycarbonate Composites having LED light conversion functions and the application thereof, XP002777913, retreived from STN Database accession No. 2012:171330.

* cited by examiner

*Primary Examiner* — Wenwen Cai
(74) *Attorney, Agent, or Firm* — Greer, Burns & Crain, Ltd.

(57) ABSTRACT

A corrosion inhibiting additive and methods of making the corrosion inhibiting additive are described. The corrosion inhibiting additive comprises a metal appended deactivated aromatic compound. The method includes reacting a metal salt with a deactivated aromatic compound to form a metal appended dichloro-diphenyl sulfone. Corrosion inhibiting coating compositions including the metal appended deactivated aromatic compound are also described.

17 Claims, No Drawings

CORROSION INHIBITING COATING ADDITIVE

This application is a U.S. National Phase under 35 U.S.C. § 371 of International Application No. PCT/US2017/060067, filed Nov. 4, 2017, which claims the benefit of U.S. Provisional Application No. 62/417,578, which was filed Nov. 4, 2016, the contents of which are hereby incorporated by reference in their entirety.

Metals or metal alloys are commonly used in aerospace, marine, auto, and many other applications. Generally, these metal or metal alloys need corrosion protection in order to effectively and safely repair aging equipment or structure. Conversion coatings and primers based on hexavalent chromium (chromium VI or chromate) have been mainstays in this effort because of their excellent corrosion inhibition, coating adhesion, and self-sealing attributes.

A conversion coating is typically formed on a metal surface using an aqueous solution of inorganic compounds, especially that of chromate or acidic phosphate. The conversion coating solution is applied to a cleaned and preferably deoxidized metal surface so that the oxidants, acids, or base in the conversion coating solution react with the metal surface. The reaction between the metal ions on the metal surface and the conversation coating causes the conversation coating to etch into the metal surface and form a very thin layer of protective oxide or phosphate film (about 0.001 to about 0.1 mil thickness). Paint or primer can be applied to the metal surfaces directly or following the application of a conversion coating.

However, prolonged exposure to hexavalent chromium can cause respiratory problems from chronic tissue irritation leading to debilitating lung disease and cancers. All forms of hexavalent chromium are recognized by the United States National Institute of Environmental Health Sciences as a Group I known human carcinogen. Thus, hexavalent chromium is coming under increased federal and state environmental regulations. Moreover, commercial use of hexavalent chromium is being restricted by the Reduction of Hazardous Substances (RoHS) directive. This directive requires manufacturers to eliminate or minimize the use of cancer-causing hexavalent chromium in conversion coatings used to protect aluminum and steel surfaces from corrosion.

Considerable efforts have made to develop alternatives to hexavalent chromate system.

US 2004/0191555 describes an anti-corrosion, non-chromate multi-layer coating. The coating includes a first layer containing particulate metal, organic liquid, thickener, and a silane binding agent, and second layer made from a powder coat composition.

U.S. Pat. No. 6,075,072 discloses corrosion preventing coating comprising a film forming binder and a plurality of microcapsules containing a corrosion inhibitor, a film forming substance, and optionally a marker die. When the coating is impacted, the microcapsules break, and the contents are released. The corrosion inhibiting materials include water insoluble amines, benzimidazole, 1-methylbenzimidazole, 1-phenylbenzimidazole, 2-phenylbenzimidazole, diethylthiophosphate, dioctylthiophosphate, thiourea, allylthiourea, phenylthiourea, 1,3-diphenylthiourea, benzotriazole, benzothiazole metal phosphates, and organophosphates metal phosphonates, metal sulfates and metal sulfonates and mixtures thereof.

U.S. Pat. No. 4,495,225 describes a corrosion resistant coating comprising an over-based alkaline earth organic sulfonate salt, a drying oil, a copper or rare earth metal drier, a zinc metal drier, a naphthenic or straight chain paraffinic oil, and petrolatum.

U.S. Pat. No. 6,419,731 discloses a non-chromate rust preventative agent. The composition includes a zirconium compound, a fluoride ion, a water-soluble resin and an aluminum salt.

Cerium ions are known to inhibit corrosion. Khaled, Electrochemical Evaluation of Environmentally Friendly Cerium Salt as Corrosion Inhibitor for Steel in 3.5% NaCl, Int. J. Electrochem. Sci., 8 (2013) 397-3987. Functional silane coatings directly modified with cerium ions were shown to provide corrosion resistance. Montemor and Ferreria, Cerium salt activated nanoparticles as fillers for silane films: Evaluation of the corrosion inhibition performance on galvanized steel substrates, Electrochimica, Acta 52 (2007) 6976-6987. However, although the cerium ions were compatible with some silane coatings, they had limited compatibility with other polymer and sol-gel chemistries. Consequently, encapsulation of cerium nanoparticles was tried, and this was shown to inhibit corrosion using encapsulation. See, e.g., Montemor, Functional and smart coatings for corrosion protection: A review of recent advances, Surf. Coat. Technol. (2014), http://dx.doi.org/10.1016/j.surfcoat.2014.06.031, 1-21; and Wang and Akid, Encapsulated cerium nitrate inhibitors to provide high-performance anti-corrosion sol-gel coatings on mild steel, Corrosion Science, 50 (2008) 11421148. http://dx.doi.org/10.1016/j.surfcoat.2014.06.031http://dx.doi.org/10.1016/j.surfcoat.2014.06.031http://dx.doi.org/10.1016/j.surfcoat.2014.06.031 However, the necessity of encapsulating the cerium to provide broad compatibility with coating systems increases the cost of the coating process.

Calcium salts of fatty acid sulfonates are commonly used corrosion inhibitors. However, they require a high concentration (more than 10%) in the final coating formulation. In addition, it is challenging to formulate them with synthetic polymers such as epoxy and polyurethane because they are not compatible with them.

However, few of the alternatives perform as well as chromium. In addition, many additives currently available as hexavalent chromium replacements evaporate at the high cure temperatures in the powder coating process.

Therefore, there is a need for improved corrosion inhibiting materials which do not contain hexavalent chromium.

DETAILED DESCRIPTION

One aspect of the invention is a corrosion inhibiting additive. In one embodiment, the corrosion inhibiting additive includes a metal appended deactivated aromatic compound.

Another aspect of the invention is a corrosion inhibiting coating. In one embodiment, the corrosion inhibiting coating includes a coating composition; and a metal appended deactivated aromatic compound. The coating composition could be, for example, a topcoat or a primer. Examples of topcoats include, but are not limited to, urethanes, urethane-epoxies, silicones, silicone-epoxies, alkyds, alkyd-epoxies, acrylics, acrylic-epoxies, polyamide, polyamide-epoxies, polyimide, polyimide-epoxies, polytetrafluoro ethylene, polyvinylidene fluoride, poly tetrafluoro vinyl ether, ceramics and combination thereof. Examples of primers include, but are not limited to, epoxy, epoxy silicone, epoxy acrylics, and combinations thereof. The corrosion inhibiting additive provides an option for additive based corrosion inhibition for solvent, water borne, and powder coatings.

Another aspect of the invention is a method of making a corrosion inhibiting additive. In one embodiment, the method includes reacting a metal salt with a deactivated aromatic compound to form a metal appended deactivated aromatic compound.

The deactivated aromatic compound has the structure:

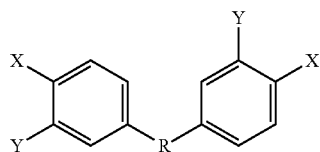

where

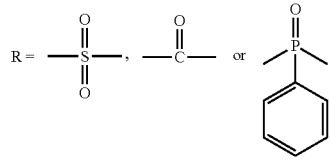

X = F, Cl, Br, I
Y = SO3H, SO3Na, SO3K, PO3H, PO3Na, PO3K, COOH, COONa or COOK

A unique deactivated aromatic compound (aromatic compounds containing electron withdrawing groups such as sulfone, ketone or phosphine oxide) paired with corrosion inhibiting element, such as cerium, has the potential to replace the chromate additive as an ecofriendly corrosion inhibitor for powder coatings. In one embodiment, a metal appended dichloro-diphenyl sulfone (DCDPS) anti-corrosion additive can reduce the corrosion susceptibility of carbon steel and other metal substrates when added to topcoats or primers.

The metal appended deactivated aromatic compound can be formed by reacting a metal salt with a functional group on the deactivated aromatic compound until the pH is neutral. The functional group is capable forming an ionic bond when treated with the metal salt. Suitable functional groups include, but are not limited to, sulfonic acid, phosphonic acid, and carboxylic acid.

Suitable metal salts include, but are not limited to, salts of cerium, lanthanum, actinide series metals, or transition metals, such as titanium, zirconium, vanadium, and the like. The counterions in the salt can be any suitable counterion, including, but not limited to, sulfate, nitrate, acetate, carboxylate, formate, phosphate, phosphonate, sulfonate, oxalate, ammonium nitrate, and carbonate.

In one embodiment, the metal appended deactivated aromatic compound is a cerium appended sulfonated DCDPS. The SDCDPS backbone has good hydrolytic and temperature stability, and resistance to UV degradation.

The oxidation/reduction capability of cerium provides an option for an ecologically friendly corrosion inhibition without the health concerns associated with chromate conversion coatings. In the presence of protons located in anodic site, the following reactions take place:

$CeO_2 + 2H^+ \rightarrow Ce(OH)_2^{2+}$ $Ce\text{-}SDCDPS + 2H_2O \rightarrow Ce(OH)_2^{2+} + H^+\text{-}SDCDPS$ $2Ce(OH)_2^{2+} + 2e^- \rightarrow Ce_2O_3 + H_2O + 2H$ The redox reaction occurs due to the oxidation-reduction capability of the $CeO_2/Ce_2O_3$. Therefore, the $CeO_2/Ce_2O_3$ mixed oxide in contact with a steel substrate would trigger passivation of the metallic material.

A reduction in flash corrosion in the further neutralized sample indicated a decrease in additive contaminants and effectiveness of raising the pH. The sample can be neutralized by further treating with bases, including, but not limited to, ammonia, triethanol amine, or triethyl amine.

In one embodiment, cerium appended sulfonated dichloro-diphenyl sulfone (SDCDPS), was made by mixing SDCDPS with cerium precursor namely cerium carbonate.

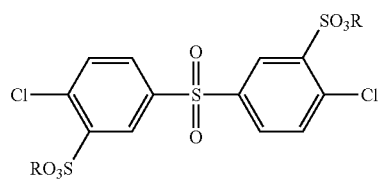

R = H, Na, K
Bis(4-chloro-3-sulfophenyl)sulfone

Neutralization with Cerium precursor

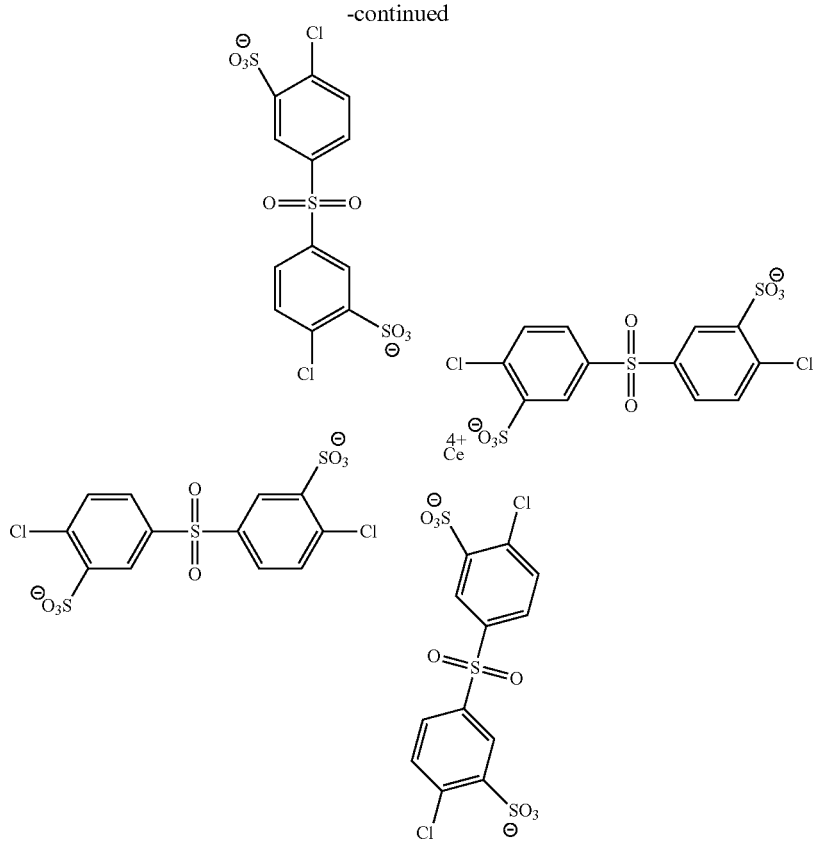

Cerium salt of bis(4-chloro-3-sulfophenyl)sulfone

Although not wishing to be bound by theory, there are two possible mechanisms which may be involved and which may be acting independently or synergistically. The cerium pendant may be acting as a passive layer and thus prevent further oxidation of metals. The oxidation of metal is the major corrosion event that happens when moisture or low molecular weight impurities such as sodium chloride, or hydrogen sulfide, penetrate through the urethane topcoat. Alternatively, the cerium may be infiltrating the pores of the topcoat and providing corrosion inhibition at the wetted metal surface. The control urethane panels showed a decrease in resistance to polarization over time, and an increase in corrosion susceptibility as the topcoat degrades.

The corrosion inhibiting additive can be coated directly onto the metal via electrodeposition or via sol-gel conversion coating or be incorporated as an additive in primers and topcoats. The corrosion inhibiting additive can be mixed into the coating composition. Suitable coating compositions include, but are not limited to, such as urethanes, urethane-epoxies, silicones, silicone-epoxies, alkyds, alkyd-epoxies, acrylics, acrylic-epoxies, polyamide, polyamide-epoxies, polyimide, polyimide-epoxies, polytetrafluoro ethylene, polyvinylidene fluoride, poly tetrafluoro vinyl ether, ceramics and combination thereof Methods of making SDCDPS and other sulfonated monomers are described in Sankir et al., Synthesis and Characterization of 3,3'-Disulfonated-4,4'=dichlorodiphenyl Sulfone (SDCDPS) Monomer for Proton Exchange Membranes (PEM) in Fuel Cell Applications, J. Applied Polymer Science, Vol. 100, 4595-4602 (2006); and U.S. Pat. No. 8,222,367, which are incorporated herein by reference.

EXAMPLES

Preparation of Cerium Salt of bis(4-chloro-3-sulfophenyl)sulfone

Example 1

30.43 grams of 4,4'-dichlorodiphenyl sulfone was added to a 250 mL reaction kettle equipped with an overhead stirrer, inlet/outlet adapter, and thermowell with a calibrated thermometer. 100 grams of Fuming Sulfuric acid (% SO3=30%) was added very slowly. The contents in the flask were slowly mixed at room temperature to ensure the DCDPS was completely dissolved. (Note: A slight exotherm was observed and the temperature increased to 45° C.). The temperature was increased (10° C. every 20 min) to 110° C. and the reaction was continued for 6 h at 110° C. After the 6 h period, the flask was gradually cooled to room temperature. 70 grams of cerium carbonate was added to 45 grams of the above reaction mixture, and the precipitate formed was collected on fritted (porosity M) filtration funnel. The precipitate was dried in an air circulated conventional oven at 60° C. for 24 hours. The product obtained was powdered using a mortar and pestle.

Example 2

10 grams of sodium salt of bis(4-chloro-3-sulfophenyl) sulfone is dissolved in 20 mL of water in a 500 mL beaker. To this mixture, 30 grams of 10 wt % ceric ammonium nitrate was added. The precipitate formed was collected on fritted (porosity M) filtration funnel. The precipitate was dried in an air circulated conventional oven at 60° C. for 24 hours. The product obtained is powdered using a mortar and pestle.

Preparation of Coating Containing Cerium Salt of bis(4-chloro-3-sulfophenyl)sulfone Example 3

8 grams of Varathane (oil-based spar urethane clear gloss coating), 1.7 grams Tiona 696 (titanium dioxide supplied by Cristal Global), 0.3 grams of cerium salt of bis(4-chloro-3-sulfophenyl)sulfone obtained from example 1, and 1.6 grams of methyl ethyl ketone were added to a plastic container. The contents were mixed well using the Siemens Speedmixer DAC 150 FVZ-K for 5 minutes. This coating product obtained was drawn onto 1010 steel panels which had been cleaned with Alconox detergent with 4 mils wet film thickness. The panels were left to air dry for 4 days and analyzed for corrosion performance using Electrochemical impedance spectroscopy and Salt fog tests.

Example 4

8 grams of Varathane (oil-based spar urethane clear gloss coating), 1.7 grams Tiona 696 (titanium dioxide supplied by Cristal Global), 0.3 grams of cerium salt of bis(4-chloro-3-sulfophenyl)sulfone obtained from Example 2, and 1.6 grams of methyl ethyl ketone were added to a plastic container. The contents were mixed well using the Siemens Speedmixer DAC 150 FVZ-K for 5 minutes. This coating product obtained was drawn onto 1010 steel panels which had been cleaned with Alconox detergent with 4 mils wet film thickness. The panels were left to air dry for 4 days. The panels were left to air dry for 4 days and analyzed for corrosion performance using Electrochemical impedance spectroscopy and Salt fog tests.

Analysis

Electrochemical impedance spectroscopy was used to determine the corrosion resistance of the coatings by subjecting the coatings to a highly corrosive environment. RTV silicone sealant was used to glue the plastic test cell to the coated panel. Once dry and fully sealed, the test cell was filled with 3.5% NaCl solution. The panel (the working electrode) was tested daily with a contact made on an uncoated portion of the substrate, a Pt counter electrode in the NaCl solution, and a SCE reference electrode between the working and counter electrodes. Water level was maintained by refilling with DI water daily.

Long term Electrochemical Impedance Spectroscopy (EIS) characterization of urethane coated steel with and without the cerium-based additive has demonstrated that the panels with the cerium additive maintained greater resistance to corrosion than the control panels without the cerium additive.

EIS results depicted that through five weeks of exposure to 3.5 wt % NaCl aqueous solution, the panels with the cerium additive showed no appreciable change in resistance to breakdown while the panels without additive exhibited a decrease in low frequency impedance over time indicative of decreasing resistance to corrosion.

Coated panels were also tested for resistance to localized corrosion via Cyclic Potentiodynamic Polarization (CPP) testing. Cerium additive coated panels were presoaked in 3.5% NaCl aqueous solution for 24 hrs prior to establishing the system's open circuit potential. Then the panel (working electrode) was cycled through a range of voltage while the response in current was monitored.

The CPP curves generated from this characterization depicted a metastable passivity but no sharp increases in current which would be indicative of a localized corrosion event. Negative hysteresis suggests that the cerium additive coating provides adequate passivation/resistance to localized breakdown and no mass loss of the substrate. The reverse scan returned to similar OCP suggesting a protected metallic substrate.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A corrosion inhibiting additive comprising:
a metal salt comprising a cationic metal moiety derived form a precursor metal salt and an anionic aromatic moiety derived from an aromatic compound, wherein the aromatic compound has a structure:

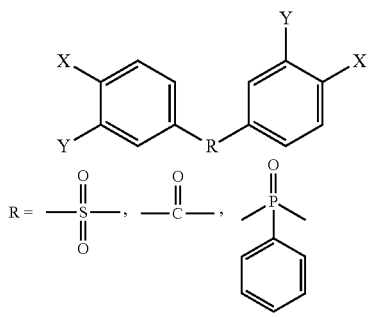

X = F, Cl, Br, I

Y = SO3H, SO3Na, SO3K, PO3H, PO3Na, PO3K, COOH, COONa, Cook wherein the metal in the precursor metal salt comprises at least one of cerium, lanthanum, actinide series metals, and metals in Groups 3-12 of the Periodic Table.

2. The corrosion inhibiting additive of claim 1 wherein the metal in the precursor metal salt comprises at least one of cerium, and lanthanum.

3. The corrosion inhibiting additive of claim 1 wherein R=sulfone.

4. The corrosion inhibiting additive of claim 1 wherein Y=SO$_3$H, SO$_3$Na, or SO$_3$K.

5. The corrosion inhibiting additive of claim 1 wherein the precursor metal salt comprises a cerium salt.

6. The corrosion inhibiting additive of claim 1 wherein the aromatic compound comprises a sulfonated dichloro-diphenyl sulfone.

7. The corrosion inhibiting additive of claim 1 wherein the precursor metal salt comprises a cerium salt and wherein the aromatic compound comprises a sulfonated dichloro-diphenyl sulfone.

8. A corrosion inhibiting coating comprising:
a coating composition; and
a corrosion inhibiting additive comprising:
a metal salt comprising a cationic metal moiety derived from a precursor metal salt and an anionic aromatic moiety derived from an aromatic compound, wherein the aromatic compound has a structure:

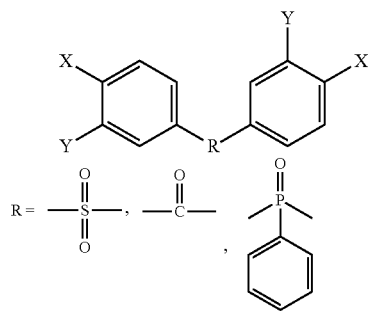

X = F, Cl, Br, I
Y = SO3H, SO3Na, SO3K, PO3H, PO3Na, PO3K, COOH, COONa, Cook wherein the metal in the precursor metal salt comprises at least one of cerium, lanthanum, actinide series metals, and metals in Groups 3-12 of the Periodic Table.

9. The corrosion inhibiting coating of claim 8 wherein the coating composition is a topcoat or a primer, wherein the topcoat comprises one selected from the group consisting of urethanes, urethane-epoxies, silicones, silicone-epoxies, alkyds, alkyd-epoxies, acrylics, acrylic-epoxies, polyamide, polyamide-epoxies, polyimide, polyimide-epoxies, polytetrafluoro ethylene, polyvinylidene fluoride, poly tetrafluoro vinyl ether, ceramics and combination thereof, wherein the primer comprises one selected from the group consisting of epoxy, epoxy silicone, epoxy acrylics, and combinations thereof.

10. A method of making a corrosion inhibiting additive comprising:
reacting a precursor metal salt with an aromatic compound having a structure:

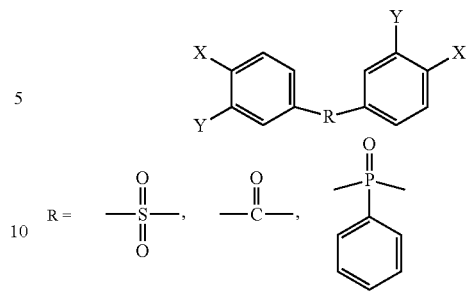

X = F, Cl, Br, I
Y = SO3H, SO3Na, So3K, PO3H, PO3Na, PO3K, COOH, COONa, COOK to form a metal salt comprising a cationic metal moiety derived from the precursor metal salt and an anionic aromatic moiety derived from the aromatic compound;
wherein the metal in the precursor metal salt comprises at least one of cerium, lanthanum, actinide series metals, and metals in Groups 3-12 of the Periodic Table.

11. The method of claim 10 wherein the metal in the precursor metal salt comprises at least one of cerium, and lanthanum.

12. The method of claim 10 wherein the counterion in the precursor metal salt is at least one of sulfate, nitrate, acetate, carboxylate, formate, phosphate, phosphonate, sulfonate, oxalate, ammonium nitrate, and carbonate.

13. The method of claim 10 wherein R=sulfone.

14. The method of any claim 10 wherein Y=SO$_3$H, SO$_3$Na, or SO$_3$K.

15. The method of claim 10 wherein the precursor metal salt comprises a cerium salt.

16. The method of claim 10 wherein the aromatic compound comprises a sulfonated dichloro-diphenyl sulfone.

17. The method of claim 10 wherein the precursor metal salt comprises a cerium salt and the aromatic compound comprises a dichloro-diphenyl sulfone.

* * * * *

UNITED STATES PATENT AND TRADEMARK OFFICE
CERTIFICATE OF CORRECTION

| | | |
|---|---|---|
| PATENT NO. | : 11,365,321 B2 | |
| APPLICATION NO. | : 16/347247 | |
| DATED | : June 21, 2022 | |
| INVENTOR(S) | : Joshua P. James and Ramanathan S. Lalgudi | |

It is certified that error appears in the above-identified patent and that said Letters Patent is hereby corrected as shown below:

In the Claims

Claim 1, Column 8, Line 28 should read "......from a precursor metal salt..."

Signed and Sealed this
Eleventh Day of July, 2023

Katherine Kelly Vidal
*Director of the United States Patent and Trademark Office*